United States Patent [19]

Landolt et al.

[11] Patent Number: 4,992,268
[45] Date of Patent: Feb. 12, 1991

[54] NOVEL SYSTEM FOR MONITORING AND CONTROLLING THE PAPAYA FRUIT FLY

[75] Inventors: Peter J. Landolt; Robert R. Heath; Herndon R. Agee, all of Gainesville, Fla.

[73] Assignee: The United States of America as represented by the Secretary of Agriculture, Washington, D.C.

[21] Appl. No.: 240,312

[22] Filed: Sep. 6, 1988

[51] Int. Cl.$^5$ ............................................. A01N 25/24
[52] U.S. Cl. ........................................ 424/77; 43/131; 43/132.1; 43/136; 424/84; 424/407; 424/410; 424/419; 544/336
[58] Field of Search ................... 424/77, 84, 407, 410, 424/419; 544/336; 43/131, 132.1, 136

[56] References Cited

U.S. PATENT DOCUMENTS

| | | | |
|---|---|---|---|
| 2,911,756 | 11/1959 | Geary | 424/84 |
| 3,030,267 | 4/1962 | Margot | 43/124 |
| 4,293,552 | 10/1981 | Miesel | 424/250 |
| 4,765,982 | 8/1988 | Ronning et al. | 424/405 |

OTHER PUBLICATIONS

Visual Attraction of the Walnut Husk Fly (Diptera: Tephritidae) to Color Rectangles and Spheres—Riedl and Hislop.
J. L. Sharp and P. J. Landolt, "Gustory and Olfactory Behavior of the Papaya Fruit Fly", *Toxotrypana curvicauda*, Gerstaecker, (Diptera:Tephritidae) in the Laboratory with Notes on Longevity, "*Journal Georgia Entomol.*", Soc.19: 176-182 (1984).
P. J. Landolt, R. R. Heath, and J. R. King, "Behavioral Responses of Female Papaya Fruit Flies", *Toxotrypana curvicauda* (Diptera: Tephritidae), to male-produced Sex Pheromone, Annals of the Entomological Society of America 78: 751-755 (1985).
P. D. Greany, H. R. Agee, A. K. Burditt, and D. L. Chambers, "Field Studies on Color Preferences of the Caribbean Fruit Fly", *Anastrepha suspensa* (Diptera: Tephritidae), *Entomol. Exp. & Appl.* 21: 63-70 (1977).
R. J. Prokopy, "Response of Apple Maggot Flies to Rectangles of Different Colors and Shades," *Environmental Entomology* 1: 720-726 (1972).
R. J. Prokopy and E. F. Boller, "Response of European Cherry Fruit Flies to Colored Rectangles," *Journal of European Entomology* 64: 1444-1447 (1971).
R. J. Prokopy and A. P. Economopoulos, "Color Responses of *Ceratitis capitata* flies," *Z. Ang. Entomol.*, 80: 434-437 (1976).
R. J. Prokopy, "Attraction of *Rhagoletis Flies* (Diptera: Tephritidae) to Red Spheres of Different Sizes," *The Canadian Entomologist* 109: 593-596 (1977).
H. Riedl and R. Hislop, "Visual Attraction of the Walnut Husk Fly (Diptera: Tephritidae) to Color Rectangles and Spheres," *Environmental Entomology* 14: 810-814 (1985).
S. Nakagawa et al., "Visual Orientation of *Ceratitis Capitata* Flies to Fruit Models," *Entomol. Exp. & Appl.*, 24: 193-198 (1978).
W. H. Reissig, B. L. Fein, and W. L. Roelofs, "Field Tests of Synthetic Apple Volatiles as Apple Maggot (Diptera: Tephritidae) Attractants," *Environmental Entomology*, 11: 1294-1298 (1982).
B. E. Mazomenos and G. E. Haniotakis, "Male Olive Fruit Fly Attraction to Synthetic Sex Pheromone Components in Laboratory and Field Tests," *Journal of Chemical Ecology*, 11: 397-405 (1985).
O. T. Jones, J. C. Lisk, C. Longhurst, and P. E. Howse, "Development of a Monitoring Trap for the Olive Fruit Fly, Dacus oleae (Gmelin) (Diptera: Tephritidae), using a Component of its Sex Pheromone as Lure," *Bull. Entomol. Res.*, 73: 97-106 (1983).

*Primary Examiner*—Merrell C. Cashion, Jr.
*Assistant Examiner*—P. L. Prater
*Attorney, Agent, or Firm*—M. Howard Silverstein; John D. Fado; Margaret A. Connor

[57] ABSTRACT

A method and apparatus for monitoring and controlling the papaya fruit fly are described. The novel system is a combination of the male papaya fruit fly sex pheromone, 2-methyl-6-vinyl-pyrazine, and a fruit mimic.

3 Claims, 4 Drawing Sheets

NOVEL SYSTEM FOR MONITORING AND CONTROLLING THE PAPAYA FRUIT FLY

BACKGROUND OF THE INVENTION

1. Field of the Invention

The present invention relates to and has among its objects the provision of a novel method and apparatus for providing in combination visual and chemical stimuli for monitoring and controlling the papaya fruit fly.

2. Description of the Art

Methods developed for monitoring, controlling, and eradicating frugivorous fruit flies (Tephritidae) have relied extensively on the use of chemical attractants. These attractants include male lures for which the behavioral basis for attraction is unknown, for example, trimedlure which is used to attract male Mediterranean fruit flies; food lures; plant host attractants; and sexual and aggregating pheromones. Sex pheromones have been demonstrated or identified for several species of Tephritidae, most involving male-produced compounds attractive to females. Successful field testing of sex pheromone baited traps have been accomplished only for the female-produced pheromone of the olive fruit fly, *Dacas oleae* (Gmelin) (Mazomenos and Haniotakis, *Journal of Chemical Ecology* 11: 397-405 (1985)). Although lures of one type or another are available for most economically important species of Tephritidae, there are few, if any, good attractants for females; more potent attractants are needed for many of these flies to aid in detecting and eradicating introduced populations.

The papaya fruit fly, *Toxotrypana curvicauda* Gerstaecker (Diptera: Tephritidae), is the principal insect pest of papaya fruit (*Carica papaya* L.) throughout the tropical and subtropical areas of the Americas. Presently, no lures or attractants are available for monitoring or controlling this insect. This tephritid, unlike many other fruit fly species, is not attracted to protein hydrolysate baits because it does not feed on protenaceaous materials as an adult, and it is not attracted to any of the identified tephritid male lures such as aqueous solutions of brown or refined sucrose or to trimedlure, methyl eugenol, cue-lure, or vinegar (Shape and Landolt, *Journal Georgia Entomolo. Soc.* 19: 176-182 (1984)). The current monitoring method used in Florida papaya groves is to visually check the grove perimeter where flies are concentrated near dusk. Satisfactory methods of control also are lacking for this pest species.

Landolt et al. (*Annals of the Enthomological Society of America* 78: 751-755 (1985)) reported that female papaya fruit flies exhibited attraction and excitatory behavior in response to male-produced volatile chemical in laboratory and wind-tunnel bioassays, which indicates that the males produce a sex pheromone.

A number of tephritid fruit flies are known to be attracted to certain colors and shapes as visual indications of foliage or fruit. It has been reported that tephritid species such as Caribbean fruit fly, *Anastrepha suspensa* (Loew); apple maggot fly, *Rhagoletis pomonella* (Walsh); European cherry fruit fly, *R. cerasi* (L.); Mediterranean fruit fly, *Ceratiotis capitata* (Wiedemann), and olive fruit fly are attracted to yellow rectangular panels, i.e. two-dimensional visual cues mimicking foliage (Greany et al., *Entomol. Exp. & Appl.* 21: 63-70, 1977; Prokopy, *Environmental Entomology* 1: 720-726, 1972; Prokopy and Boller, *Journal of Economic Entomology* 64: 1444-1447, 1971, and Prokopy and Economopoulos, *Z. Ang. Entomol.* 80: 434-437, 1976). Painted spheres, i.e., three-dimensional visual cues mimicking host fruit, have been reported as attractive to the apple maggot fly (dark red spheres); walnut hust fly, *R. completa* Cresson, (green spheres); and Mediterranean fruit fly (black or yellow spheres) (Prokopy, *The Canadian Entomologist* 109: 593-596, 1977; Riedl and Hislop, *Environmental Entomology* 14: 810-814, 1985, and Nakagawa et al., *Entomol. Exp. & Appl.* 24: 193-198, 1978). Some species have been trapped with a combination of visual stimuli of fruit or foliage and chemical (non-pheromonal) lures. Reissig et al., *Environmental Entomology* 11: 1294-1298, 1982, trapped apple maggot flies using synthetic apple volatiles baited with red spheres. Riedl and Hislop, supra, reported that the addition of ammonium carbonate as a food olfactory stimulus enhanced the response of walnut hust flies to yellow rectangles and green spheres but at a loss of selectivity for the target fly. Nakagawa et al., supra, reported that the addition of the chemical lure, trimedlure, to yellow rectangles or black spheres, enhanced attraction for male Mediterranean fruit flies. The only report of the combination of a visual mimic and a pheromonal lure is by Jones et al., *Bull. Entomol. Res.* 73: 97-106, 1983, who report the use of a component of the female-produced olive fruit fly sex pheromone and yellow panels (foliage mimic) to trap male flies. To date, no attractant or monitoring method is available for the papaya fruit fly, and methods are needed to reduce crop losses caused by this insect.

SUMMARY OF THE INVENTION

The invention provides, for the first time, a system for monitoring and controlling the papaya fruit fly. The method and apparatus of the invention comprise a unique combination of visual and chemical stimuli which not only attracts the papaya fruit fly but induces it to land so that it can be trapped, killed or otherwise controlled. We have surprisingly discovered that by combining a visual stimulus which mimics the host fruit with the newly discovered male-produced papaya fruit fly sex pheromone, 2-methyl-6-vinyl-pyrazine (2,6-MVP), papaya fruit flies are not only attracted to the visual stimulus but are caused to land on it in preference to host fruit. Our system is the first that attracts females of a fruit fly species with sex pheromone. This is also the first use of a combination visual fruit mimic and sex pheromone.

Attempts to trap papaya fruit flies in the field with 2,6-MVP using conventional traps were unsuccessful. Although the pheromone appeared to attract female papaya fruit flies in field tests, the flies did not land on the traps baited with the pheromone, but instead landed on nearby fruit. Laboratory wind-tunnel studies also indicated low rates of contact or landing by female papaya fruit flies in response to 2,6-MVP despite very close approaches. Use of the visual mimic alone without the pheromone resulted in significantly fewer and economically insufficient catches of the flies. Surprisingly, the combination of a visual fruit mimic and 2,6-MVP results in an effective system to monitor and control papaya fruit flies. With the combination of the invention, the papaya fruit fly females land on the visual stimulus rather than on nearby fruit as occurs when the pheromone is used alone.

This modification of female fruit fly behavior was unexpected. Prior to the invention, little was known of the actual behavior involved in tephritid sex pheromone attraction, or the role of sex pheromone in tephritid mate-finding and close-range courtship behavior. Further, there was no recognition of an association between sexual attraction (mate-finding) and attraction to the host plant (host attraction). The requirement that specific visual stimuli to promote landing and capture of papaya fruit flies attracted by the pheromone was not heretofore recognized. The prior art teaches that sexual behavior of fruit flies is independent of attraction to the host plant. For example, as discussed above, the prior art teaches that many fruit flies are attracted to yellow as a positive response to foliage, and that some species utilize visual characteristics of host fruit, e.g., three-dimensional spheres, to locate oviposition sites, but with no indication of any association with mate-finding (sexual attraction) by female flies. Published combinations of painted spheres and chemical lures such as described by Riedl and Hislop, supra, demonstrate an association in tephritid fruit flies between adult feeding behavior and visual attraction to fruit. Adults feed on yeast and bacterial colonies on the surface of ripe fruit. This behavior is independent of sexual attraction and host finding and does not suggest the required combination for trapping female papaya fruit flies of sexual attraction and plant host attraction or the response of female papaya fruit flies to a papaya fruit mimic lacking in food materials. Also, unlike many other tephritids, the papaya fruit fly does not feed on these materials as adults. Published combinations of visual cues and chemical lures for which the behavioral basis for attraction is unknown, e.g., trimedlure (Nakagawa et al., supra), does not provide information about the behavioral responses of female papaya fruit flies and the requirements of a trapping system. Further, trimedlure differs from 2,6-MVP in that it is a potent attractant of male Mediterranean fruit flies which causes the males to be attracted to and land so that they can be trapped in any conventional trap, not just by use with a fruit mimic as is required in the invention.

Although sex pheromones have been identified for a number of tephritid fruit flies, as discussed above successful field testing of sex pheromone baited traps for frugivorous fruit flies (Tephritidae) has been accomplished only for the female-produced pheromone of the olive fruit fly (Mazomenos and Haniotakis, supra). Combination of the major component (spiroacetal) of the female-produced sex pheromone and yellow panels (foliage mimic) to capture olive fruit fly males (Jones et al., supra) does not suggest the requirements to trap female papaya fruit flies using a male-produced pheromone. The olive fruit fly is unlike other tephritids in that it utilizes a female sex pheromone that attracts males for mating, and the published research does not provide information about the behavioral ecology of papaya fruit fly females. Further, as with the other art it teaches one to expect that insects utilize female-produced male attractants independent of hosts or other resources.

The novel combination of visual and chemical stimuli of the invention provides a tool for detection of the papaya fruit fly and provides a means for population control and population density estimation of this pest. By placing a control agent in the vicinity of where the flies land, for example, by coating the visual stimulus with an adhesive material, the flies can be trapped. Similarly, use of a killing agent such as a pesticide for the papaya fruit fly in combination with the invention provides a means for controlling the flies. The usefulness of the invention in attracting papaya fruit flies when applied to a locus of females and inducing them to land suggests the following economic applications: (1) the detection of infestation outbreaks; (2) the monitoring of existing adult populations in order to predict future infestation levels to better schedule (and reduce) treatment with conventional pesticides; and (3) the control of reproduction in adult populations by attracting a demographically significant portion of the female population for subsequent destruction or sterilization.

A particular advantage of the invention is that it includes a male-produced pheromone which attracts female fruit flies. Because the invention results in the trapping or death of the female papaya fruit fly, it directly removes her reproductive potential from the field, effectively saving a number of fruit from infestation.

Another advantage of the invention is that allows detection of populations and changes in populations of papaya fruit flies and provides a means to control papaya fruit flies in papaya plantings to reduce or prevent fruit losses caused by this pest.

In accordance with this discovery it is an object of the invention to provide a combination of visual and chemical stimuli which attracts papaya fruit flies and induces them to land.

It is also an object of the invention to provide a method of monitoring the presence of papaya fruit fly populations in papaya groves and provide a means to control populations through female trapping or destruction before they infest fruit.

Other objects and advantages of the invention will become readily apparent from the ensuing description.

DETAILED DESCRIPTION OF THE INVENTION

Figure 1:
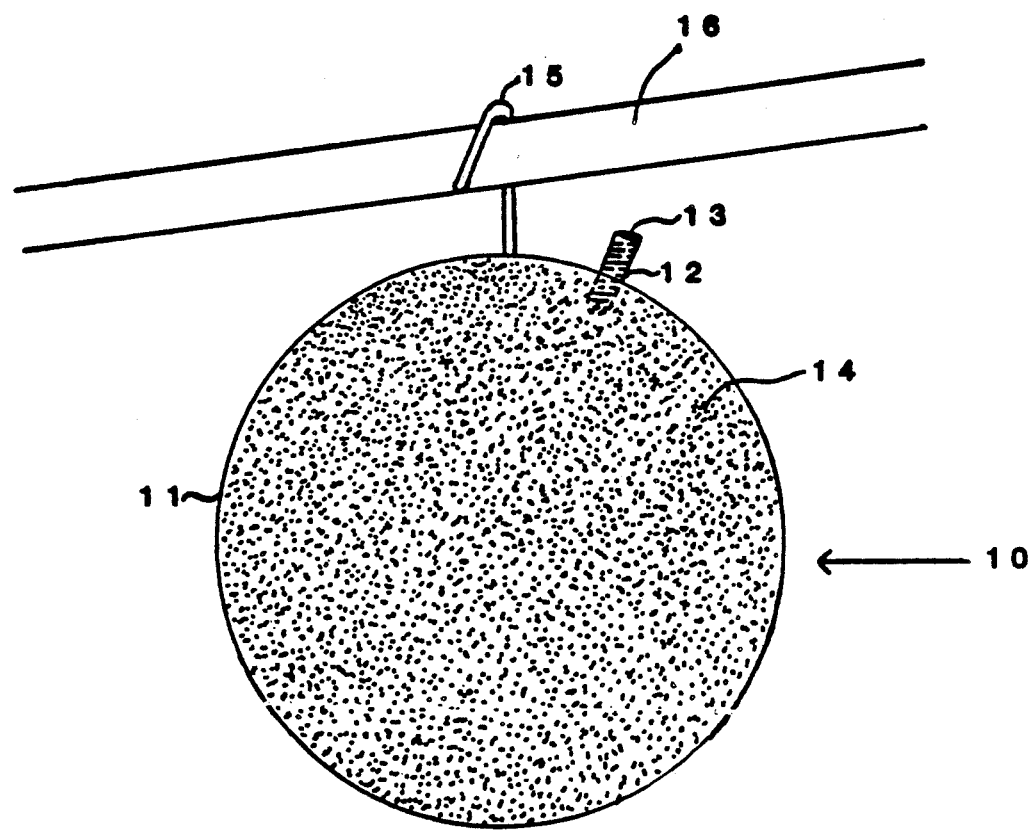
FIG. 1 shows one embodiment of the apparatus of the invention.

The method and apparatus of the invention provide a unique combination of a visual stimulus characteristic of the host fruit and a chemical stimulus. It is theorized that through the artificial duplication of the natural chemical and visual stimuli that the papaya fruit fly females can be deceived into alighting on a trap. This unique combination provides, for the first time, a system wherein the papaya fruit flies are optimally attracted and induced to land so that monitoring or controlling of the flies can be carried out. The attraction of papaya fruit flies to pheromone to locate hosts in addition to locating mates was unexpected and adds greatly to the value of the trap through the removal of mated fruit flies ready to oviposit in papaya fruit.

There are several features of the invention which influence its functioning and efficiency. These include the size, shape, and color of the visual stimulus, and the type, release rate, and point of release of the chemical stimulus. The performance of the invention when placed in a papaya tree is dictated partly by the attractiveness of the pheromone lure and partly by the short range response of the fly to visual characteristics of the visual stimulus versus that of papaya fruit on the tree.

Our research shows that the optimum visual stimulus is one which mimics the host fruit, e.g., papaya, preferably the unripe fruit.

Size and Shape. The recommended shape is spherical; other shapes which are functional include ovoid to oblong-ovoid. With regard to the visual stimulus, we have found that the diameter of the visual stimulus should be in the range of 5–20 cm. The recommended diameter is 13–15 cm. The effect of sphere diameter on the percentages of attracted female papaya fruit flies hovering within 15 cm or landing on green spheres of different diameters in a flight tunnel bioassay is described in detailed below in Example 2 and FIG. 3.

Color. We have found that the most effective color is one which provides contrast with papaya tree foliage (which is yellow-green) and which reflects green wavelengths (520–570 nm range). The recommended color is dark green. The effectiveness of this color (with the shape, discussed in detail above) as a short range visual attractant appears to be due to a combination of hue (reflectance) and lack of brightness contrasting with background foliage which is brighter in color, thus making the shape more apparent. Thus it is recommended that the visual stimulus should have some reflectance in the 520–570 nm range and little or no reflectance elsewhere. Other colors of visual stimuli which function to cause papaya fruit flies to land and be trapped, but are less effective than the recommended color as described above, include, black, also combinations of green and other hues.

Type of Chemical Stimulus. The chemical stimulus useful in our invention is the heretofore unknown male-produced sex pheromone of the papaya fruit fly, 2,6-MVP. The synthesis of 2,6-MVP to obtain the compound in pure or substantially pure form is described in detail below in Example 1. As discussed above, this compound is ineffective as a trapping or controlling agent when used alone; however, in the invention, it functions as a long range attractant to attract the flies over a long distance to the visual stimulus which in turn induces the female flies to land so that they can be trapped or otherwise controlled.

Release Rate of the Chemical Stimulus. 2,6-MVP is used in combination with the visual stimulus in an effective amount. An effective amount is defined as that quantity of compound which provides a release rate of the compound that attracts papaya fruit fly females to the location of a bait at a rate significantly higher than females are attracted to a nonbaited location. Factors such as insect population density, temperature, wind velocity, and release rate will influence the response of the flies and thus the actual number of flies trapped. Factors such as temperature, wind velocity and release substrate will influence release rate. The amount of compound in a particular set of circumstances that will provide a release rate within the effective range can readily be determined by a dose response field test as described in Example 3 below. We have found that in using the apparatus of the invention described below in Example 3 and shown in FIG. 1 in Florida papaya groves, an effective release rate is from about 75 to 1500 ng per hour per apparatus with the optimum at about 1000 ng per hour per apparatus.

Point of Release of the Chemical Stimulus. The chemical stimulus must be released sufficiently close to the visual stimulus so that the papaya fruit flies are attracted sufficiently close to the visual stimulus such that the flies are induced to land on the visual stimulus rather than surrounding papaya fruit. We have found that the recommended release point of the chemical stimulus be within about 3 cm from the surface of the visual stimulus.

Formulation of the Chemical Stimulus. Typically, 2,6-MVP is applied to the release substrate undiluted or in solution in hexane or other suitable carrier. Volatilization can be retarded by inclusion of a material that has a higher molecular weight than 2,6-MVP and that does not interfere with the activity of the pheromone. Slow release may also be effected by encapsulation or absorption into a porous substrate.

Uses of the Invention

Use of the invention as a monitoring and detection tool can be carried out in several ways. One method is to coat the visual stimulus with a trapping agent, for example, an adhesive material which captures the attracted papaya fruit flies. When used as a detection or monitoring agent, the catch is tabulated to determine size and location of infestation. Economic use of appropriate pest management systems can then be determined. The method of trapping the flies can also serve as a control method. This use of the invention with a outer sticky coating is described in detail below in Example 3.

Other uses of the invention as a control agent can be carried out by using the invention in combination with insecticides or other control agents. The invention is used to attract the flies and induce them to land and subsequently or simultaneously the insects are exposed to insecticides which control the flies. An effective amount of the insecticide is used, that is an amount that is lethal for an exposed insect or at least sublethal but sufficient to incapacitate the insect in regard to mating activity. Illustrative of the wide variety of insecticides which may be used with the invention are dichlorvos and naled.

Another method to control papaya fruit flies using the invention is to detect the location and boundaries of localized fruit fly infestations and employ in the area chemosterilants, bioregulator agents, parasites or predators, or other biological control agents for the papaya fruit fly.

The apparatus and method of the invention will next be described with reference to FIG. 1.

FIG. 1 depicts the trapping system 10 which includes a fruit mimic, shown as sphere 11, and tube 12 for containing phenomone 13. Tube 12 has a sealed bottom end attached to sphere 11 and has an open end for releasing pheromone in close proximity to sphere 11. Pheromone 13 (2,6-MVP) is placed within tube 12. In this embodiment, the surface of sphere 11 is coated with an adhesive material 14 to catch flies that land on the sphere. Wire 15 attached to sphere 11 is used to hang the trapping system from papaya tree branch 16.

In an alternate embodiment, sphere 11 is impregnated with papaya fruit fly insecticide or microcapsules containing insecticide are attached to sphere 11 to kill or incapacitate flies that land on the sphere. A catch basin may be placed below to catch the incapacitated flies.

EXAMPLES

The following example are intended only to further illustrate the invention and are not intended to limit the scope of the invention which is defined by the claims.

EXAMPLE 1

Figure 2:
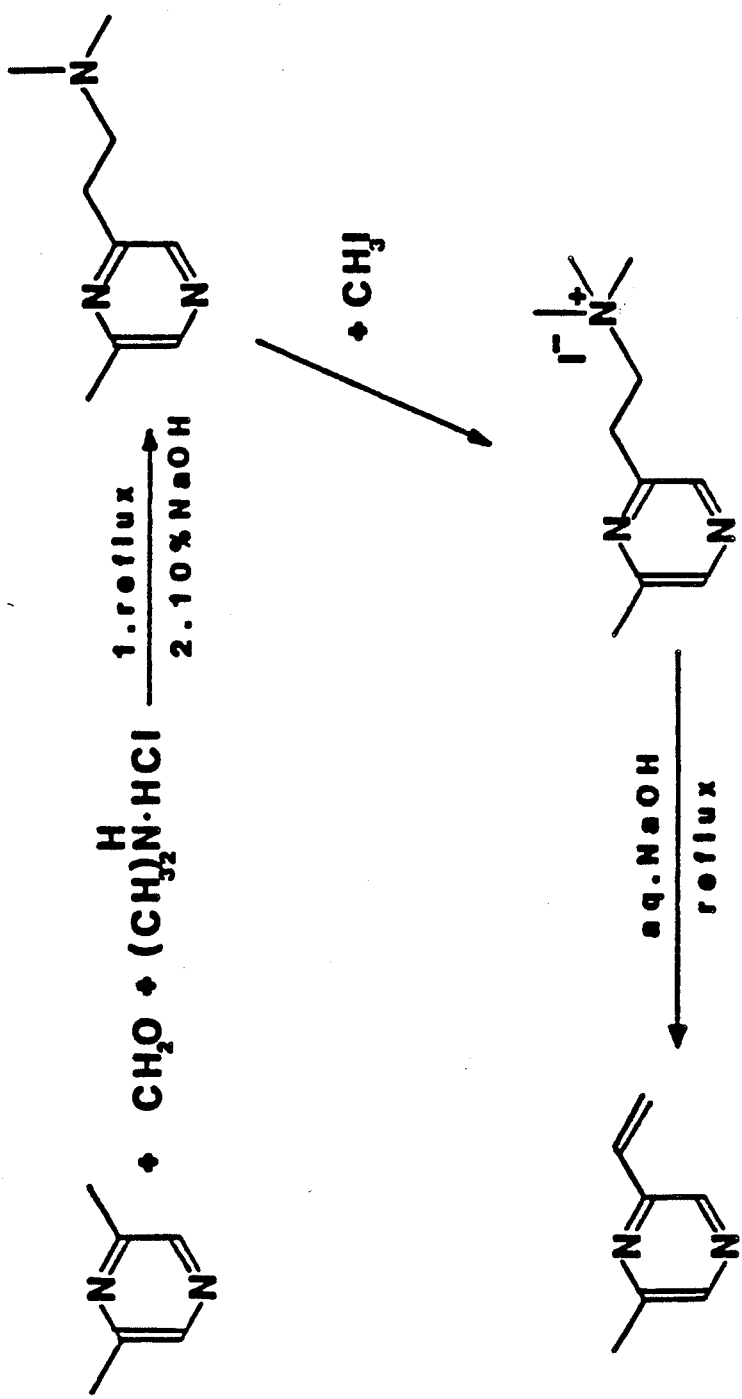
FIG. 2 shows a procedure for synthesizing 2,6-MVP.

Synthesis of 2,6-MVP. 2,6-MVP was synthesized from 2,6-dimethylpyrazine employing a Hoffman exhaustive methylation procedure and modification described by Kamal et al., *Journal of Organic Chemistry* 27: 1363–1366 (1962) as shown in FIG. 2.

2-Methyl-6-dimethylaminoethylpyrazine. A mixture of 2,6-dimethylpyrazine (Pyrazine Specialities, Inc., Atlanta, Georgia, containing 2%, 2,5-isomer) (15.5 g) and dimethylamine hydrochloride (13.0 g) was heated until it began refluxing, and then formaldehyde (22.5 g as 38% aqueous solution) was added over a 30-min period. The resulting solution was refluxed for 2 hours. The solution was cooled to room temperature and diluted with water, made basic by the addition of 10% aqueous solution of sodium hydroxide, and extracted with chloroform. After removing the solvent, distillation of the residue gave 7.8 g of 2-methyl-6-dimethylaminoethylpyrazine with 5% of the 2,5-isomer (33% yield), 120°–126° C./12 mm Hg.

6-Methylpyrazylethyl-trimethylammonium Iodide. Methyl iodide (6.4 g) was added to a stirring solution of 2-methyl-6-dimethylaminoethylpyrazine (4.6 g) in 20 ml ofanhydrous ether under argon atmosphere. The mixture was allowed to stand overnight at room temperature. A yellow solid formed was filtered and washed with a small amount of ether to give 6.0 g of the quaternary iodide salt (70% yield). This hygroscopic compound was subjected to the next step without further purification.

2-Methyl-6-vinylpyrazine. The quaternary ammonium iodide (6.0 g) was dissolved in 40 ml of water. Then, 1.7 g of sodium hydroxide was added and the mixture was refluxed for 1 hour. The resulting solution was cooled to room temperature and extracted with chloroform. The chloroform solution was dried over $Na_2SO_4$ and evaporated carefully at atmospheric pressure. Microdistillation at 12 mm Hg gave 2.4 g of 2-methyl-6-vinylpyrazine (74% yield) with 5% of the 2,5-isomer. Pure 2-methyl-6-vinylpyrazine (100% purity) for bioassay was obtained by high performance liquid chromatography purification on a silica gel column. Capacity factors (k') (Schram, *The LDC Basic Book on Liquid Chromatography*, Milton Roy Co., St. Petersburg, Florida (1980)) of 2-methyl-6-vinylpyrazine and its 2,5-isomer were 2.0 and 3.2, respectively. MS (m/z; 37; (43), 52 (72), 54 (26), 94 (26), 120 (M+, 100); IR ($cm^{-1}$, $CCl_4$ solution); 3105 (m), 3045 (m), 2940 (m), 1545 (s), 1456 (m), 1422 (s), 1395 (s), 1380 (m), 1275 (s), 1260 (s), 1228 (s), 1178 (s), 1160 (s), 1020 (s), 986 (s), 940 (s), 930 (s), 880 (s), PMR ($C_6D_6$); 8.16 (1H, s), 7.98 (1H, s), 6.50 (1H, dd, J=17.4 Hz, 10.5 Hz), 6.33 (1H, dd, J=17.4 Hz, 1.6 Hz), 5.22 (1H, dd, J=10.5 Hz, 1.6 Hz), 2.08 (3H, S).

EXAMPLE 2

Papaya Fruit Fly Rearing and Handling. Papaya fruit flies used in laboratory and field cage studies were obtained as mature larvae from field-collected papaya fruit in Dade County, Florida. Larvae pupated in paper cartons (500-ml) of heat-sterilized potting soil. Emerged flies were sorted by sex daily and were kept in aluminum frame and fiberglass screen cages (30 by 30 by 30 cm) with sugar water on cotton. Males and females were kept in separate rooms to minimize female exposure to male-produced pheromone. Males used were 3 to 16 days old, while females used were 6 to 16 days old. Females become reproductively mature and sexually receptive by day 6. Flies with damaged wings or that flew with difficulty were excluded from the experiments.

Flight Tunnel Bioassays. The flight tunnel used for the bioassays was a plexiglass tube (43 cm diameter by 2.4 m long). Air was pulled through the tunnel at 0.2 m/s. Lighting was provided by eight 34-watt fluorescent bulbs arranged directly above the tunnel. Room and tunnel temperatures were 24.5±0.5° C. with humidity ranging from 45 to 65%. Formulated pheromone was placed on an aluminum wire hanger positioned near the center of the upwind end of the tunnel, and flies were released from 50-ml polystyrene vials at the downwind end of the tunnel. Smoke plumes generated in the tunnel neared the tunnel walls about three-fourths of the way downwind (0.6 m from the downwind end).

Effect of Sphere Size on Landing by Pheromone-attracted Papaya Fruit Fly Females. The effect of sphere size on landing by pheromone-attracted papaya fruit fly females was evaluated in a flight tunnel described above. Styrofoam spheres in available sizes (5.1, 7.6, 10.2, and 12.7 cm diameter) were painted green and were mounted singly on a wire near the center of the upwind end of the flight tunnel. Glass capillary tubing that released ca. 600 ng of 2,6-MVP per hour was mounted on the top of the sphere for the bioassay. Release rates of 2,6-MVP from glass capillaries were determined by analysis of volatiles collected from capillaries loaded with 2,6-MVP. Briefly, this method consisted of placing the capillaries in a collection chamber through which purified (charcoal filtered) air was introduced at a rate that provided a windspeed of 22 cm/s over the capillary. The effluent was collected using charcoal filters described by Tumlinson et al., In B.A. Leonhardt & M. Beroza (eds.), *Insect Pheromone Technology: Chemistry and Applications*, ACS Symposium Series 190 (1982)). The filters were extracted using 75 $\mu$l of methylene chloride and 20 $\mu$l of hexane. An internal standard was added, and the samples were analyzed using SBP1 (Supelco) fused silica capillary column (50 by 0.25 mm i.d.) installed in a Hewlett Packard 5890 gas chromatograph. Chromatography conditions were as follows: initial temperature=60° C., split off for 30 s, oven temperature increased at 20° C./min after 30 s, to a final temperature of 175° C.; the linear flow velocity of the helium carrier gas was 18 cm/s. The output of the flame ionization detection was interfaced to a Nelson 4000 data station.

Mature unmated females were released signly at the down wind end from a 65-ml plastic vial and were given 2 minutes to respond. They were scored for flight, plume-tracking (zig-zagging unwind flight within the plume), close-range hovering (casting within 15 cm of source), and landing. Bioassays was conducted in a randomized complete block design, with sphere sizes randomized daily and five females tested sequentially for each o the sphere sizes. The set of 20 fly bioassays was replicated 10 times, on 10 different days. Percentage response data were subjected to regression analysis.

Figure 3:
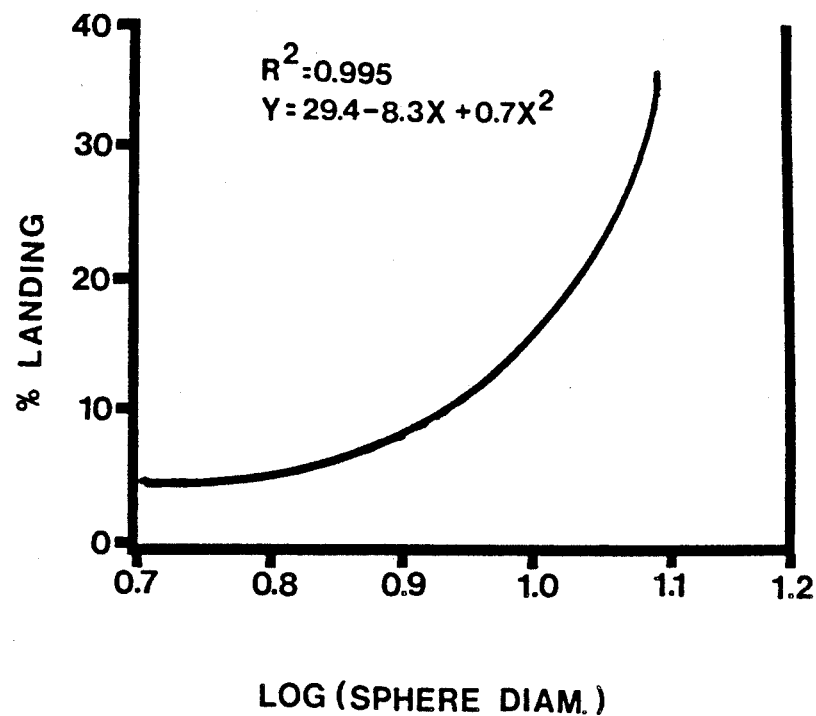
FIG. 3 shows the percentages of attracted females hovering within 15 cm or landing or green spheres of different diameters in a flight tunnel bioassay.

The results are shown in FIG. 3. The percentage of attracted female papaya fruit flies (those that zig-zagged unwind) that landed on spheres in the flight tunnel increased with sphere size, from 4.8% landing on 5-cm diameter spheres to 36.7% landing with 12.7-cm diameter spheres.

EXAMPLE 3

Field Trapping Test. The combination visual and chemical stimuli was accessed for ability to attract and trap papaya fruit flies in the field. Styrofoam spheres (12.7 cm diameter) were painted with white latex paint followed by UN-78 Garden Green Spray Enamel (New York Bronze Powder Co., Inc., Elizabeth, NJ). The outside of the sphere was coated with the a sticky substrate "Tack-Trap." 2,6-MVP, synthesized as described in Example 1, was placed in 50-mm-long glass capillary tubing having an inside diameter of 0.38 or 0.60 mm. After sealing one end of the tubing, pheromone was introduced by a syringe to a height of 30 mm. 2,6-MVP was used with the sticky spheres at four release rates selected to test a range possibly occurring in nature (70, 140, 300, and 900 ng/h). These release rates were provided by using combinations of 0.38 or 0.60-mm i.d. glass capillary tubing loaded with 2,6-MVP. A male papaya fruit fly releases 2,6-MVP at ca. 80 ng/h. The tubes were forced into the spheres near the top, but with the one end protruding 1 to 2 cm from the sphere surface. The sticky spheres with pheromone in capillary tubing (denoted as traps) were hung with wire hangers in papaya trees, attached to leaf petioles near fruit clusters.

The traps were set up in a randomized complete block design, with each of four blocks comprised of the five release rate treatments. Each block was set up in one of four papaya groves in the Redlands area of Dade County, Florida. Traps were placed in border rows where fly activity was highest and fruit damage was greatest, with five papaya trees (ca. 7.5 m) between traps. Traps were checked and maintained (cleaned of flies and sticky coating replaced when necessary) three times per week for 2 weeks. Trap catch data were subjected to ANOVA, and treatment means were separated using Duncan's multiple range test (Duncan, *Biometrics* 11: 1–42 (1955), at $P \leq 0.05$).

Figure 4:
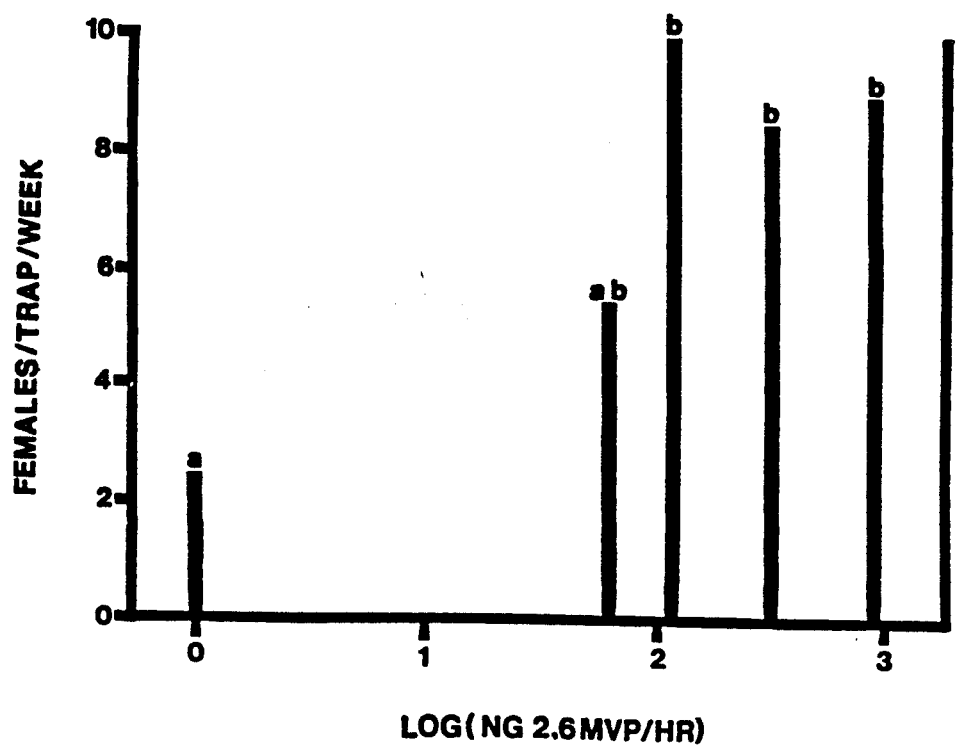
FIG. 4 shows the numbers of female papaya fruit flies caught per trap per week on 12.7 cm diameter green sticky spheres baited with different release rates of 2,6-MVP in papaya groves.

The results are shown in FIG. 4. Bars with the same letter are not significantly different by Duncan's multiple range test, supra. Both sexes of papaya fruit flies were caught consistently on traps with all pheromone release rates studied, including the control. However, significantly more females were captured on traps baited with 2,6-MVP pyrazine at release rates of 140, 300, or 900 ng/h, than on control traps. Catches of males in pheromone-baited traps were not significantly greater than in control traps. Totals of 149 females and 69 males were captured on traps during this test.

Another field test was carried out as follows: Traps used were 12.7 cm diameter polypropylene spheres painted dark green (UN-78 Garden Green Spray Enamel, New York Bronze Powder Co, Elizabeth, NJ) coated with "Tangle Foot" (Tangle Foot Co., Grand Rapids, MI). Synthetic 2,6-MVP prepared as described in Example 1 was placed in glass capillary tubing as described above to provide lures with different release rates of pheromone. Lures were mounted in wooden dowels, in turn mounted in holes in the spheres, with the lure opening 2–3 cm above the sphere surface.

Eight treatments were compared, with lures providing release rates of 0, 76, 152, 228, 323, 640, 960, and 1520 2,6-MVP/hour (empirically determined in the laboratory). Pheromone baited traps were set up in blocks each comprised of all eight treatments randomized within a row of papaya trees. Traps within blocks were 5 meters apart and 1.3 to 2 meters above the ground. Traps were hung from papaya leaf petioles near fruit clusters in trees in the outside borders of papaya groves. On four dates: April 6, April 27, May 21, and June 2, four blocks were set up. Flies were counted and traps cleared daily or every other day for 21, 2, 3, and 2 days respectively.

Figure 5:
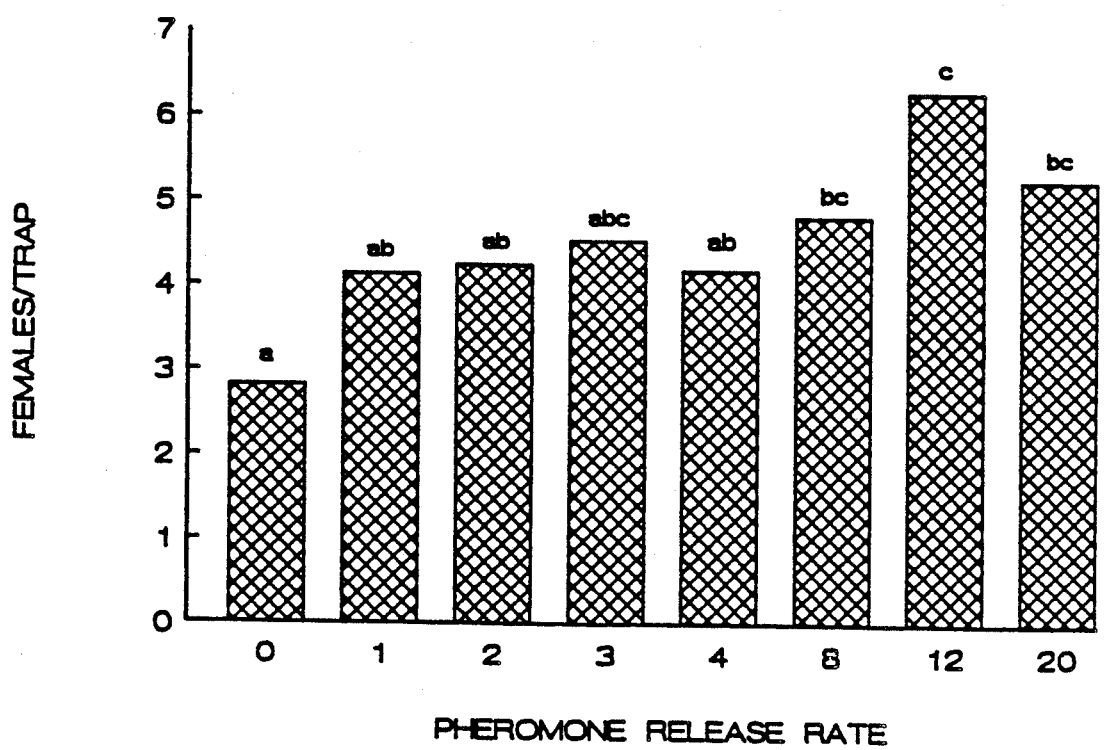
FIG. 5 shows the numbers of female papaya fruit flies caught per trap on 12.7 cm diameter green sticky spheres baited with different release rates of 2,6-MVP in papaya groves. One male equivalent (ME) equals ca. 80 ng/h.

The results are shown in FIG. 5. Catches of female papaya fruit flies on traps baited with 2,6-MVP release rates of 8, 12, and 20 male equivalents (ME, ca. 80 ng/h) were significantly greater than on unbaited fruit mimic traps (ANOVA, Duncan's multiple range test, supra, P=0.05). Bars with the same letter are not significantly different by Duncan's multiple range test, supra. Greatest trap catches were obtained with 2,6-MVP released at 12 ME (960 ng/h).

EXAMPLE 4

The following example illustrates that 2,6-MVP is ineffective in trapping papaya fruit flies when placed in conventional traps.

A. Tests Using "Pherocon" 1 C Traps (Zoecon Corp., Palo Alto, CA). In these tests 2,6 MVP formulated in rubber septa were compared to unbaited traps as controls. In the first test five replicate sets of traps were placed in a papaya field Oct. 9, 1985, at 4 p.m. Traps were hung from papaya leaf petioles and placed 15 meters apart. Septa were pinned to small pieces of styrofoam placed in the center of the sticky liner of each trap. Traps were checked at 6 p.m. on October 9 and 2:30 p.m. on Oct. 10. No flies were trapped. This test was repeated November 14, and 15, 1985, using the same methods but with the simultaneous release of 80 sexually mature female papaya fruit flies in the field. Traps were checked after 24 hr and 1 female papaya fruit fly was caught. A concurrent run test in another papaya field, using "Phenocon" traps baited with 2,6-MVP formulated in glass capillary tubing yielded no flies trapped.

B. Trapping papaya fruit flies was attempted using modified "Pherocon" 1C traps with the tops removed, baited with 2,6-MVP in glass capillary tubing, providing release rates of 0, 20, 80, 300, and 700 ng/hr. Three blocks of traps each with all 5 treatments were set up Dec. 9, 1985 in a Dade County papaya field. Traps were placed as described previously and were checked daily for 4 days. One male papaya fruit fly was caught in a trap with the 80 ng 2,6-MVP/hr formulation.

C. Trapping papaya fruit flies was attempted using "Rebell" yellow sticky vane traps. Five treatments (the same 5 release rates of 2,6-MVP from glass capillary tubing) were compared in 3 blocks set up in 3 papaya fields in Guatemala. Traps were checked daily for 5 days. Three papaya fruit flies were caught; 1 male and 1 female on traps baited with 80 ng 2,6-MVP/hr and 1 male on a trap baited with 700 ng 2,6-MVP/hr.

It is understood that the foregoing detailed description is given merely by way of illustration and that modification and variations may be made therein without departing from the spirit and scope of the invention.

Having thus described the invention, we claim:

1. An apparatus for monitoring or controlling the papaya fruit fly which comprises a green or black sphere having an adhesive material on the surface of said sphere, wherein said sphere is in combination with an effective attractant amount of substantially pure 2-methyl-6-vinylpyrazine as a papaya fruit fly sex pheromone.

2. The apparatus of claim 1 wherein said pheromone is in a pheromone release substrate which is attached to said sphere.

3. A method for monitoring or controlling the papaya fruit fly which comprises placing in an area where papaya fruit flies are to be attracted a green or black sphere having an adhesive substance on the surface of said sphere and placing in operative relation to said sphere an effective attractant amount of substantially pure 2-methyl-6-vinylpyrazine as a papaya fruit fly sex pheromone such that papaya fruit flies are attached to and induced to land on said fruit mimic.

* * * * *